(12) United States Patent
Fukao et al.

(10) Patent No.: US 7,232,928 B2
(45) Date of Patent: Jun. 19, 2007

(54) STABILIZATION METHOD OF CYCLOALKANONE OXIME

(75) Inventors: Masami Fukao, Ritto (JP); Noriaki Tanaka, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 10/995,253

(22) Filed: Nov. 24, 2004

(65) Prior Publication Data

US 2005/0119479 A1 Jun. 2, 2005

(30) Foreign Application Priority Data

| Nov. 28, 2003 | (JP) | ............................. 2003-399147 |
| Dec. 22, 2003 | (JP) | ............................. 2003-424583 |
| Mar. 31, 2004 | (JP) | ............................. 2004-103180 |

(51) Int. Cl.
 *C07C 209/90* (2006.01)
(52) U.S. Cl. ..................... 564/2; 564/8; 564/9; 564/12; 564/253; 564/264
(58) Field of Classification Search ..................... 564/2
 See application file for complete search history.

(56) References Cited

U.S. PATENT DOCUMENTS 2,964,563 A * 12/1960 Bost et al. ..................... 564/2

| 4,931,592 | A | 6/1990 | Fuchs et al. |
| 5,315,039 | A | 5/1994 | Kajikuri et al. |
| 2003/0013916 | A1 | 1/2003 | Fukao et al. |

FOREIGN PATENT DOCUMENTS

| EP | 0550965 A2 | | 7/1993 |
| EP | 1270548 A1 | | 1/2003 |
| GB | 977812 | | 12/1964 |
| GB | 1056124 | * | 1/1967 |
| JP | 47-41909 B | | 10/1972 |

OTHER PUBLICATIONS

Database CAPLUS on STN, Acc. No. 2002:3703, Song et al., Fudan Xuebao, Yixue Kexueban (2001), 28(6), p. 486-489 (abstract).*
English language abstract of JP 50 003317 B (Feb. 3, 1975).

* cited by examiner

*Primary Examiner*—Brian Davis
(74) *Attorney, Agent, or Firm*—Birch, Stewart, Kolasch & Birch, LLP

(57) ABSTRACT

Cycloalkanone oxime is stabilized by a method comprising bringing the cycloalkanone oxime into contact with at least one compound selected from the group consisting of oxoacids, oxoacid salts, oxoacid esters, oxoacid amides and oxides of boron or phosphorus. In accordance with the invention, the thermal stability of cycloalkanone oxime can be improved.

16 Claims, No Drawings

STABILIZATION METHOD OF CYCLOALKANONE OXIME

BACKGROUND OF THE INVENTION

1. Field of the Present Invention

The present invention relates to a stabilization method of a cycloalkanone oxime.

2. Description of the Related Art

Since a cycloalkanone oxime is thermally instable, a variety of methods of improving its thermal stability have been proposed, such as a method of allowing an alkali metal or alkaline earth metal, or an oxide, a hydroxide or an alcoholate of an alkali metal, alkaline earth metal, zinc or aluminum to be existed in a gasification region of a cycloalkanone oxime (see, Japanese Patent Application Publication No. 47-41909);

a method of washing a molten cycloalkanone oxime with an aqueous ammonium sulfate solution and keeping pH at 4.5 to 5.8 (see, Japanese Patent Application Laid-Open No. 2-193957);

a method of allowing ammonia or a lower alkyl amine to be existed in an cycloalkanone oxime (see, Japanese Patent Application Laid-Open No. 5-186409); and a method of washing a cycloalkanone oxime solution with water or an aqueous basic solution and a method of passing a cycloalkanone oxime solution through a weakly alkaline ion exchange resin (see, Japanese Patent Application Laid-Open No. 2003-34674).

SUMMARY OF THE INVENTION

However, the thermal stability of the cycloalkanone oxime has not necessarily been sufficient by these conventional methods. One of objects of the present invention is to provide a method of improving the thermal stability of the cycloalkanone oxime.

Based on the results of intensive investigations, present inventors have found that the above-mentioned object can be achieved by bringing the cycloalkanone oxime into contact with an oxide of boron or phosphorus or an oxoacid compound. Also, the inventors have found that it is effective to improve the thermal stability of the cycloalkanone oxime by controlling the concentration of a transition metal such as iron, nickel or the like in cycloalkanone oxime or its solution at a temperature of about 50° C. or higher. Based on these findings, the present invention has been accomplished.

The present invention provides a stabilization method of a cycloalkanone oxime comprising bringing the cycloalkanone oxime into contact with at least one compound selected from the group consisting of oxoacids, oxoacid salts, oxoacid esters, oxoacid amides and oxides of boron or phosphorus.

Also, the present invention provides a stabilization method of a cycloalkanone oxime, which comprises the step of controlling the concentration of a transition metal to be about 30 ppm by weight or lower at a temperature of about 50° C. or higher.

In accordance with the present invention, the thermal stability of the cycloalkanone oxime can be improved.

PREFERRED EMBODIMENTS OF THE INVENTION

In the present invention, a cycloalkanone oxime is stabilized. As a result, even if stocked, the cycloalkanone oxime may contain fewer amounts of impurities such as condensation compounds of the cycloalkanone oxime or its derivatives such as tar components.

Examples of the cycloalkanone oxime to be stabilized are cyclopentanone oxime, cyclohexanone oxime, cyclooctanone oxime and cyclododecanone oxime. If necessary, two or more of these cycloalkanone oximes may be stabilized together. The cycloalkanone oxime can be produced by, for example, a method of reacting cycloalkanone with hydroxylamine or its salt; a method of conducting photo-nitrosation of a cycloalkane; and a method of reacting cycloalkanone with ammonia and hydrogen peroxide in the presence of a catalyst such as titanosilicates.

Cycloalkanone oxime is sometimes handled in a high temperature condition. For example, some cycloalkanone oximes are in the solid state at room temperature, and therefore, are heated in many cases at storage or transportation in order to have the cycloalkanone oxime in a molten state and make its handling easy. Specifically, the heating is sometime conducted to have a temperature of melting point or higher, for example, a temperature of about 90° C. or higher for cyclohexanone oxime. Also, even if the cycloalkanone oxime is in a liquid state at a normal temperature or the cycloalkanone oxime is in the form of a solution thereof with a solvent, the cycloalkanone oxime may be heated, for example, to a temperature of 50° C. or higher at storage or transportation, in order to decrease its viscosity and make its handling easy. Further, at the time of evaporating the cycloalkanone oxime (such as the time of purification with distillation, the time of preparation of a raw material gas for a vapor phase Beckmann rearrangement, and the like), a cycloalkanone oxime may be heated to a boiling point or higher, (for example, to a temperature of about 195° C. or higher for cyclopentanone oxime, and to a temperature of about 205° C. or higher for cyclohexanone oxime, under a normal pressure). Also, at the time of reducing the pressure or being accompanied with a low boiling point gas, the cycloalkanone oxime may be heated at 150° C. or higher. In the present invention, the cycloalkanone oxime can be stabilized even in such a high temperature condition.

In one of the methods of the present invention, a cycloalkanone oxime is stabilized by bringing the cycloalkanone oxime into contact with at least one oxoacid compound selected from the group consisting of oxoacids, oxoacid salts, oxoacid esters and oxoacid amides of boron or phosphorus; and/or with at least one compound selected from the group consisting of oxides of boron or phosphorus. Alternatively, in another one of methods of the present invention, a cycloalkanone oxime is stabilized by controlling the concentration of a transition metal therein (or in a solution thereof) to be about 30 ppm by weight or lower. The former and latter stabilization methods may be carried out, simultaneously.

An example of the oxides of boron to be used for the present invention may be diboron trioxide ($B_2O_3$), and examples of the oxoacids of boron may be orthoboric acid ($H_3BO_3$), metaboric acid ($HBO_2$), hypoboric acid ($H_4B_2O_4$), and their condensed acids. Additionally, the oxides and oxoacids of boron may contain elements other than boron and oxygen in their skeleton structures, if necessary.

Examples of the oxides of phosphorus to be used for the present invention may be tetraphosphorus hexaoxide ($P_4O_6$; named also as phosphorus trioxide), tetraphosphorus decaoxide ($P_4O_{10}$; named also as phosphorus pentoxide), and examples of the oxoacids of phosphorus may be orthophosphoric acid ($H_3PO_4$), metaphosphoric acid ($HPO_3$), phosphonic acid ($H_3PO_3$; named also as phosphorous acid), phosphinic acid ($H_3PO_2$; named also as hypophosphorous acid), and their condensed acids. Additionally, the oxides and oxoacids of phosphorus may contain elements other than phosphorus and oxygen in their skeleton structures, if necessary.

The oxoacid salts of boron or phosphorus to be used in the present invention may be normal salts obtained by replacement of all of the protons of the above-mentioned oxoacids of boron or phosphorus with metal ions and/or ammonium ions; or may be acidic salts obtained by replacement of a partial (i.e., one or more but not all) protons of the above-mentioned oxoacids of boron or phosphorus with metal ions and/or ammonium ions. Preferable examples of the metal ions are metal ions of Group I elements in a periodic table (such as sodium and potassium (in Group IA)); metal ions of Group II elements (such as calcium and magnesium (in Group IIA)); metal ions of Group IV elements (such as titanium and zirconium (in Group IVA)); and metal ions of Group XII elements (such as zinc (in Group IIB)). Also, the ammonium ions may be protonated ammonia or may be protonated aliphatic, alicyclic or aromatic amines, which may be primary, secondary, or tertiary amines, or quaternary ammonium ions.

The esters of oxoacids of boron or phosphorus to be used in the present invention may be oxoacid esters obtained by replacement of all of the hydroxyl groups of the above-mentioned oxoacids of boron or phosphorus with alcohol residues (that are the groups obtained by removing hydrogen atoms bonded to oxygen atoms from alcohols), or may be oxoacid esters obtained by replacement of a partial hydroxyl groups of the above-mentioned oxoacids of boron or phosphorus with alcohol residues.

The oxoacid amides of boron or phosphorus to be used in the present invention may be oxoacid amides obtained by replacement of all of the hydroxyl groups of the above-mentioned oxoacids of boron or phosphorus with amine residues (that are the groups obtained by removing hydrogen atoms bonded to nitrogen atoms from amines), or may be oxoacid amides obtained by replacement of a partial hydroxyl groups of the above-mentioned oxoacids of boron or phosphorus with amine residues.

The alcohol residues of the oxoacid esters may be aliphatic, alicyclic or aromatic alcohol residues, which may be primary, secondary, or tertiary alcohol residues. Also, the amine residues of the oxoacid amides may be aliphatic, alicyclic or aromatic amine residues, which may be primary or secondary amine residues.

In stabilizing the cycloalkanone oxime by bringing it into contact with oxides or oxoacid compounds of boron or phosphorus, at least one compound selected from the above-described oxides or oxoacid compounds of boron or phosphorus is sufficient to be used, and if necessary, two or more kinds of the compounds may be used in combination. The amount of the boron or phosphorus oxides or oxoacid compound to be used may be in the range of from about 0.0001% by mole to about 1% by mole, and is preferably in the range of from about 0.001% by mole to about 0.5% by mole, based on the cycloalkanone oxime. Such a boron or phosphorus compound may be used while being dissolved or suspended in water or an organic solvent.

For example, in the case of using an oxoacid of boron, an oxoacid of phosphorus, a salt of an oxoacid of boron or a salt of an oxoacid of phosphorus while being dissolved in water, the concentration of such a boron or phosphorus compound (which is a total concentration of the compounds when two or more of the compounds are used) in the resulting aqueous solution may be adjusted to be in the range of from about 0.01 mol/L to about 3 mol/L, and is preferably in the range of from about 0.05 mol/L to about 2 mol/L. The amount of such an aqueous solution (containing the boron or phosphorus compound) to be used may be in the range of from about 10 parts by weight to about 1,000 parts by weight, and is preferably in the range of from about 50 parts by weight to about 200 parts by weight, based on 100 parts by weight of the cycloalkanone oxime.

When an aqueous solution, an organic solvent solution, or a suspension of the boron or phosphorus compound as described above is utilized, the cycloalkanone oxime to be subjected to the contact treatment is preferably in form of a liquid. For example, the cycloalkanone oxime may be subjected to the contact treatment in the molten form thereof, or in the form of an organic solvent solution thereof. That is, the stabilization in the present invention may be carried out in the state that the cycloalkanone oxime is in a molten state or is dissolved in an organic solvent. It is noted that the contact treatment in the present invention can be suitably employed in vaporizing a cycloalkanone oxime in which a cycloalkanone oxime remaining in a liquid state without being vaporized is subjected to the contact treatment.

The above-mentioned organic solvent may be those separable from water, and examples thereof are aliphatic hydrocarbons such as hexane, heptane and octane; alicyclic hydrocarbons such as cyclopentane, cyclohexane and methylcyclohexane; aromatic hydrocarbons such as benzene, toluene and xylene; halogenated aliphatic hydrocarbons such as dichloromethane and 1,2-dichloroethane; halogenated aromatic hydrocarbons such as chlorobenzene and dichlorobenzene; ketones such as ethyl methyl ketone, isobutyl methyl ketone; and esters such as ethyl acetate and isopropyl acetate. Two or more of them may be used, if necessary. Among them, aromatic hydrocarbons are preferred. The amount of such a solvent to be used may be in the range of from about 1 parts by weight to about 1,000 parts by weight, is preferably in the range of from about 50 parts by weight to about 300 parts by weight, and is more preferably in the range of from about 50 parts by weight to about 200 parts by weight, based on 100 parts by weight of the cycloalkanone oxime to be dissolved therein.

Bringing a cycloalkanone oxime into contact with the above-mentioned boron or phosphorus compound can be employed in a variety of ways. For example, in the case of storing, transporting, or evaporating the cycloalkanone oxime, the above-mentioned compound may previously be introduced into a storage tank, a transportation pipe, an evaporator or the like before introducing the cycloalkanone oxime thereto; or the above-mentioned compound may be added simultaneously with introduction of the cycloalkanone oxime thereto; or the above-mentioned compound may be added after introducing the cycloalkanone oxime thereto.

When the cycloalkanone oxime is in a liquid state (such as in a solution thereof), the cycloalkanone oxime may be brought into contact with the boron or phosphorus compound, for example, in a way such that an aqueous solution of the boron or phosphorus compound and the cycloalkanone oxime solution may be mixed with each other while stirring or shaking.

After the contact of the above-mentioned aqueous solution of the boron or phosphorus compound with the cycloalkanone oxime solution, the resulting mixture may be separated into an oil layer and a water layer, and the cycloalkanone oxime or its solution may be recovered in the oil layer.

The contact treatment may be repeated a plurality of times, if necessary. The cycloalkanone oxime to be treated may be washed with water before and/or after the contact treatment. Also, if insoluble matters are produced in the contact treatment or the washing with water, such insoluble matters are preferably removed by filtration.

The temperature of the contact treatment may be about 20° C. or higher, and is preferably in the range of from about 20° C. to 100° C. When a molten cycloalkanone oxime is treated, the treatment temperature may be the melting temperature of the cycloalkanone oxime or higher.

The stabilization method of the present invention improves thermal stability of cycloalkanone oxime, and therefore, can be effectively employed in the case of handling (e.g., storing, transporting or evaporating) the cycloalkanone oxime at a high temperature, such as a temperature of about 50° C. or higher, which may be a temperature of about 90° C. or higher. Especially, when the cycloalkanone oxime is evaporated, the stabilization method of the cycloalkanone oxime of the present invention may be employed advantageously as the pretreatment step for the evaporation, the cycloalkanone oxime is often handled at a temperature higher than the temperature at which the cycloalkanone oxime is stored or transported.

As described above, the inventors of the present invention have found that the thermal stability of the cycloalkanone oxime can be improved by the contact treatment with the boron or phosphorus compound. In addition, the inventors of the present invention also have found that the thermal stability of the cycloalkanone oxime can be improved by controlling the concentration of a transition metal component, e.g., a metal and its oxide, salt (except for oxoacid salt of boron or phosphorus) or complex of a metal in Group V to XI in a periodic table (Groups VA to VIIA, VIII and IB), such as iron, nickel and chromium, since they can inhibit the thermal stability of the cycloalkanone oxime.

Since such a transition metal component is sometimes contained in a material (e.g., a stainless steel) constituting a reactor, a tank, a pipe and the like for producing cycloalkanone oxime, the transition metal component may be eluted in the produced cycloalkanone oxime and thus may inhibit the thermal stability of the cycloalkanone oxime. When the cycloalkanone oxime is evaporated, the above-mentioned transition metal component can be concentrated and can exist in a high concentration in the remaining cycloalkanone oxime left behind after evaporation, and thus may inhibit further the thermal stability of the cycloalkanone oxime. To stabilize the cycloalkanone oxime containing the transition metal component in such a manner, it is effective to carry out the above-mentioned contact treatment with the boron or phosphorus compound; or to control the concentration of the transition metal component to a concentration low enough to avoid adverse effects by the transition metal component; or carry out both of the contact treatment and the controlling of the concentration of the transition metal component.

When the cycloalkanone oxime contains the above-mentioned transition metal component, the boron or phosphorus compound may be used in an amount of about 1 mole time to about 1,000 mole times, is preferably used in an amount of about 3 mole times to 300 mole times, and is more preferably used in an amount of about 5 more times to 100 mole times, as much as that of the transition metal component, to stabilize the cycloalkanone oxime.

In order to further improve the thermal stability of the cycloalkanone oxime, it is preferred to use a material which is free from such a transition metal component described above as a material for the reactor, the tank, the pipe and the like; and/or to use a material lined with glass or a fluorocarbon resin at the portions which may contact with the cycloalkanone oxime.

In another method of the present invention, the cycloalkanone oxime is stabilized by controlling the concentration of each transition metal to be about 30 ppm by weight or lower in the cycloalkanone oxime (or its solution) at a high temperature, for example, at a temperature of about 50° C. or higher. For example, the concentration of an iron component may be controlled to be about 30 ppm by weight or lower.

When the cycloalkanone oxime contains a plurality of transition metals, it is more preferred to control the total concentrations of the transition metals in the cycloalkanone oxime (or its solution) to be about 30 ppm by weight or lower.

As the transition metals whose concentration(s) are to be controlled, the above-mentioned metals are exemplified and especially, the control of iron concentration (and copper concentration, if any) is apparently more effective to stabilize the cycloalkanone oxime.

As described above, the cycloalkanone oxime to be stabilized may be dissolved in an organic solvent, or may be cycloalkanone oxime itself.

Examples of the organic solvent to be used here may be the same organic solvents exemplified above. The amounts of them to be used are also the same as described above.

When a liquid containing cycloalkanone oxime is handled at a temperature of about 50° C. or higher, the concentration of a transition metal such as iron in the liquid may be controlled to be about 30 ppm by weight or lower, is preferably controlled to be about 10 ppm by weight or lower, and is more preferably controlled to be about 5 ppm by weight or lower, to stabilize the cycloalkanone oxime in the liquid. By such a controlling, the thermal stability of the cycloalkanone oxime can be improved, which makes it possible to stably handle the cycloalkanone oxime.

There is no particular lower limit of the concentration of the transition metal to be controlled. The less the concentration be, the more stabilized the cycloalkanone oxime becomes. It may be preferred to control the transition metal having a concentration of about 0.1 ppm by weight or higher.

The transition metal can exist in a cycloalkanone oxime in the form of metal, or in the form of ion, oxide, salt, or complex of the metal. The amount of the transition metal in the cycloalkanone oxime tends to increase more as the period of time in which the cycloalkanone oxime contacts with a material containing the transition metal is longer, and/or as the temperature at which the cycloalkanone oxime contacts with the material is higher. The larger amount of the transition metal seems to further worsen the thermal stability of the cycloalkanone oxime.

It is noted that since stainless steel SUS 304 comprises iron, nickel and chromium, the cycloalkanone oxime having a history of contact with the stainless steel SUS 304 may possibly contain nickel and chromium in addition to iron. Also, since stainless steel SUS 316 comprises iron, nickel, chromium and molybdenum, the cycloalkanone oxime having a history of contact with the stainless steel SUS 316 may possibly contain nickel, chromium and molybdenum in addition to iron. When the cycloalkanone oxime containing such transition metal components in addition to iron is handled, the concentration of at least one concentration of the transition metal components in the cycloalkanone oxime, as well as the concentration of iron, is preferably controlled. Especially, since stainless steels such as SUS 304 and SUS 316 are commonly used as iron-containing materials, it is preferred to control the concentrations of nickel and chromium, together with the concentration of iron. In this case, the total of the respective concentrations of iron, nickel and chromium in the cycloalkanone oxime or in the liquid containing the cycloalkanone oxime may be controlled to be in the range of from about 30 ppm by weight or lower, is preferably in the range of from about 10 ppm by weight or lower, and is more preferably in the range of from about 5 ppm by weight or lower. The transition metals to be controlled are transition metals, each having a concentration of at least 0.1 ppm by weight. More particularly, for example, iron having a concentration of about 0.1 ppm by weight or more, nickel having a concentration of about 0.2 ppm by weight or more, and chromium having a concentration of 0.4 ppm by weight in a cycloalkanone oxime may be controlled in the present invention. The concentrations of the transition metals can be measured by, for example, atomic absorption spectrometry, inductively coupled plasma (ICP) mass spectrometry, ion chromatography, colorimetric method and the like. Depending on the state of the cycloalkanone oxime having the transition metals, analysis values correlated with the concentrations of the transition metals can be used as substitution values for the concentrations of the transition metals. The analysis value can be obtained by various calorimetric analysis methods, for example, thermogravimetry (TG), differential thermal analysis (DTA), differential scanning calorimetry (DSC) and accelerated rate calorimetry (ARC).

In order to decrease an iron concentration in a liquid containing a cycloalkanone oxime to a prescribed value (30 ppm) or lower, it is preferred to shorten the period of contact time of the liquid with the iron-containing material and also to maintain a temperature as low as possible at the time when the liquid contacts with the iron-containing material. It is also effective to use an iron-free material, for example, a material made of a metal in Groups IVA, IIIB and IVB in a periodic table, such as zinc, tin, aluminum and titanium, glass, a resin and an iron-containing material lined with these metals, glass and a resin such as a fluorocarbon resin, in place of the iron-containing material for a reactor and the like.

In the case of evaporating a cycloalkanone oxime (for example, in the case of distillation for purification of the cycloalkanone oxime or preparing a raw material gas of the cycloalkanone oxime to be subjected to vapor phase Beckmann rearrangement), a liquid containing the cycloalkanone oxime is often used as a feed raw material, which may be exposed under a high temperature condition, and therefore, the method of the present invention of controlling the concentration of the transition metal is effectively applied. In this case, together with a cycloalkanone oxime-containing gas, a can liquid (a concentrated liquid) such as a tower bottom liquid of a distillation tower is typically produced, and the iron component seems to be concentrated in the can liquid in many cases. Therefore, in this case, it is appropriate to control the iron concentration in the can liquid. In order to maintain the iron concentration in the can liquid to a prescribed value or lower, it is preferred that the iron concentration in liquid containing the cycloalkanone oxime as a feed raw material is measured, and then the upper limit of the concentration ratio of the can liquid is decided based on the measured value. Also, when the amount of the iron component in the feed raw material is too small to be measured, the iron concentration in the can liquid may be measured several times, to carry out the operation of the evaporating of the cycloalkanone oxime so as not to have an iron concentration lager than the prescribed value in the can liquid.

The invention being thus described, it will be apparent that the same may be varied in many ways. Such variations are to be regarded as within the spirit and scope of the invention, and all such modifications as would be apparent to one skilled in the art are intended to be within the scope of the following claims.

The entire disclosure of the Japanese Patent Applications Nos. 2003-399147 filed on Nov. 28, 2003; 2003-424583 filed on Dec. 22, 2003; and 2004-103180 filed on Mar. 31, 2004, including specifications, claims and summaries, are incorporated herein by reference in their entirety.

EXAMPLES

The present invention is described in more detail by following Examples, which should not be construed as a limitation upon the scope of the present invention.

Example 1A

To 100.1 g of cyclohexanone oxime [purity: 98.9% by weight (measured by gas chromatography); containing iron (8 ppm by mole), chromium (0.4 ppm by mole) and nickel (0.8 ppm by mole) (measured by atomic absorption spectrometry)], was added 0.5 g of 1% by weight of an aqueous orthoboric acid solution. The resulting mixture was heated in a glass flask at a temperature of 200° C. for 5 hours under a nitrogen gas flow, and then was vacuum-distilled until no fraction distilled was observed. The amount of a liquid (tar component) remaining in the flask after the distillation was 5.89 g (which was 5.9% by weight based on 100% cyclohexanone oxime).

The amount of the tar component corresponds to the amount of the compounds generated by the decomposition of the cyclohexanone oxime. Therefore, the more stabilized the cyclohexanone oxime is, the smaller the amount of the tar component is measured after the heating and distillation procedure.

Example 2A

The same procedure as in Example 1A was conducted except that 0.5 g of 1% by weight of an aqueous orthophosphoric acid solution was used, instead of using 0.5 g of 1% by weight of an aqueous orthoboric acid solution. As a result, the amount of a liquid (tar component) remaining in the flask after the distillation was 3.89 g (which was 3.9% by weight based on 100% cyclohexanone oxime).

Example 3A

The same procedure as in Example 1A was conducted except that 0.5 g of 1% by weight of an aqueous phosphorous acid solution was used, instead of using 0.5 g of 1% by weight of an aqueous orthoboric acid solution. As a result, the amount of a liquid (tar component) remaining in the flask after the distillation was 4.28 g (which was 4.3% by weight based on 100% cyclohexanone oxime).

Example 4A

The same procedure as in Example 1A was conducted except that the amount of the cyclohexanone oxime used was changed from 100.1 g to 100.08 g, and 0.67 g of a 1% by weight of a methanol solution containing trimethyl orthoborate was used instead of using 0.5 g of 1% by weight of an aqueous orthoboric acid solution. As a result, the amount of a liquid (tar component) remaining in the flask after the distillation was 7.42 g (which was 7.4% by weight based on the cyclohexanone oxime; and was 7.5% by weight based on 100% cyclohexanone oxime).

Comparative Example 1A

The same procedure as in Example 1A was conducted except that the amount of the cyclohexanone oxime used was changed from 100.1 g to 110 g, and 0.5 g of a 1% by weight of an aqueous sodium hydroxide solution was used instead of using 0.5 g of 1% by weight of an aqueous orthoboric acid solution. As a result, the amount of a liquid (tar component) remaining in the flask after the distillation was 37.7 g (which was 34.3% by weight based on the cyclohexanone oxime; and was 34.7% by weight based on 100% cyclohexanone oxime).

Comparative Example 2A

The same procedure as in Example 1A was conducted except that the amount of the cyclohexanone oxime used was changed from 100.1 g to 100.29 g, and 0.5 g of 1% by weight of an aqueous orthoboric acid solution was not used. As a result, the amount of a liquid (tar component) remaining in the flask after the distillation was 28.01 g (which was 27.9% by weight based on the cyclohexanone oxime; and was 28.2% by weight based on 100% cyclohexanone oxime).

Reference Example 1B

A cyclohexanone oxime [purity: 89.2% by weight (measured by gas chromatography); containing iron (24 ppm by mole) (measured by atomic absorption spectrometry)] (100 g) was heated in a glass flask at a temperature of 200° C. for 5 hours in nitrogen gas flow, while being stirred by a stirrer coated with a fluororesin, and then was vacuum-distilled at a temperature of 158° C. under a pressure of 0.4 Torr (53 Pa) until no fraction distilled was observed. The amount of a liquid (tar component) remaining in the flask after the distillation was 57.1 g (which was 57.1% by weight based on the cyclohexanone oxime; and was 64.0% by weight based on 100% cyclohexanone oxime).

Example 1B

The same cyclohexanone oxime (100 g) as that used in Reference Example 1B was dissolved in a toluene (100 g), and a 1 mol/L of an aqueous orthophosphoric acid solution (100 g) was added thereto. The resulting mixture was stirred at a temperature of 75° C. for 1 hour, and then was separated into an oil layer and a water layer. To the oil layer, was added water (100 g), and the resulting mixture was stirred at a temperature of 75° C. for 1 hour, which was then filtered to remove a trace of insoluble matters. The resulting mixture was separated into an oil layer and a water layer. The oil layer was concentrated under a reduced pressure to remove the toluene. As a result, a cyclohexanone oxime (98 g) was recovered. The cyclohexanone oxime was heated in the same manner as in Reference Example 1B, and was then vacuum-distilled. The amount of a liquid (tar component) remaining in the flask after the distillation was 19.4 g (which was 19.8% by weight based on the recovered cyclohexanone oxime).

Reference Example 2B

A cyclohexanone oxime [purity: 98% by weight (measured by gas chromatography); containing iron (8 ppm by mole) (measured by atomic absorption spectrometry)] (100 g) was heated and was then vacuum-distilled in the same manner as in Reference Example 1B. The amount of a liquid (tar component) remaining in the flask after the distillation was 35.7 g (which was 35.7% by weight based on the cyclohexanone oxime).

Example 2B

The same procedure as in Example 1B was conducted except that the same cyclohexanone oxime (100 g) as that used in Reference Example 2B was used instead of using the same cyclohexanone oxime (100 g) as that used in Reference Example 1B, and a 1 mol/L of an aqueous orthoboric acid solution (100 g) was used instead of using the 1 mol/L of an aqueous orthophosphoric acid solution (100 g). As a result, a cyclohexanone oxime (98 g) was recovered. The cyclohexanone oxime was heated in the same manner as in Reference Example 1B and was then vacuum-distilled. The amount of a liquid (tar component) remaining in the flask after the distillation was 7.3 g (which was 7.4% by weight based on the recovered cyclohexanone oxime).

Comparative Example 1B

The same procedure as in Example 2B was conducted except that 1 mol/L of an aqueous orthoboric acid solution (100 g) was not used. As a result, a cyclohexanone oxime (98 g) was recovered. The cyclohexanone oxime was heated in the same manner as in Reference Example 1B and was then vacuum-distilled. The amount of a liquid (tar component) remaining in the flask after the distillation was 29.8 g (which was 30.4% by weight based on the recovered cyclohexanone oxime).

Comparative Example 2B

The same procedure as in Example 2B was conducted except that 0.1 mol/L of an aqueous sodium hydroxide solution (100 g) was used instead of using the 1 mol/L of aqueous orthoboric acid solution (100 g). As a result, a cyclohexanone oxime (98 g) was recovered. The cyclohexanone oxime was heated in the same manner as Reference Example 1B and was then vacuum-distilled. The amount of a liquid (tar component) remaining in the flask after the distillation was 12 g (which was 12.2% by weight based on the recovered cyclohexanone oxime).

Examples 1C to 4C and Comparative Example 1C

A molten cyclohexanone oxime which has been prepared by ammoximation reaction of cyclohexanone) as a raw material, a methanol and nitrogen were continuously supplied at a ratio by weight of cycloalkanone oxime/methanol/nitrogen=5/9/1 into a falling film evaporator, to continuously produce a gas containing cyclohexanone oxime, methanol and nitrogen, while continuously discharging can liquids. Specifically, the supply amount of the raw material was controlled by changing the evaporation pressure and the evaporation temperature in the ranges of 950 Torr (0.125 MPa) or lower and of from 140° C. to 160° C., respectively, to discharge can liquids each containing iron, nickel, and chromium in the concentration shown in Table 1 below.

Each can liquid was subjected to accelerated rate calorimetry (ARC) measurement (disclosed in "Sumitomo Chemical Co., Ltd. Report" 1989-I, Sumitomo Chemical Co., Ltd., pp. 61–81, issued in 1989) to measure heat generation initiating temperature (which is a temperature at which the self-heat generation rate reaches 0.02° C./minute) and TMR (Time to Maximum Rate; which is a period of time in which self-heat generation rate under a thermal insulation condition (at a temperature of at least 150° C.) becomes the maximum. The results are shown in Table 1.

A cyclohexanone oxime with low thermal stability tends to decompose even at a low temperature for a short period of time, and therefore, tends to show a large self-heat generation rate (corresponding a decomposition rate of cyclohexanone oxime) even at a low temperature and/or show the maximum of the self-heat generation rate for a short period of time under a thermal insulation condition. As a result, the cyclohexanone oxime with low thermal stability tends to show a low heat generation initiating temperatures and shorter TMR. In the same manner, the more stabilized the cyclohexanone oxime in the can liquids are, the higher heat generation initiating temperatures and longer TMRs are measured.

TABLE 1

| Example | Iron concentration (ppm by weight) | Nickel concentration (ppm by weight) | Chromium concentration (ppm by weight) | Heat generation initiating temperature (° C.) | TMR (hour) |
|---|---|---|---|---|---|
| Supplied raw material | <0.1 | <0.2 | <0.4 | 176.3 | 67 |
| Example 1 | 1.6 | 0.3 | <0.4 | 146.7 | 7.7 |
| Example 2 | 2.6 | 0.4 | 0.6 | 138.0 | 4.8 |
| Example 3 | 10 | 1.9 | 1.4 | 126.7 | 1.5 |
| Comparative Example 1 | 61 | 4.8 | 4.5 | 79.6 | 0.95 |

What is claimed is:

1. A stabilization method of a cycloalkanone oxime comprising bringing the cycloalkanone oxime into contact with at least one compound that is selected from the group consisting of oxides of boron and oxides of phosphorus.

2. A stabilization method of a cycloalkanone oxime comprising bringing the cycloalkanone oxime into contact with at least one compound that is selected from the group consisting of oxoacids of boron, oxoacids of phosphorus, oxoacid salts of boron, oxoacid salts of phosphorus, oxoacid esters of boron, oxoacid esters of phosphorus, oxoacid amides of boron and oxoacid amides of phosphorus, and wherein the at least one compound is used in an amount of about 0.0001% by mole to about 1% V mole based on the cycloalkanone oxime.

3. The method according to claim 1, wherein the at least one compound is used in an amount of about 0.0001% by mole to about 1% by mole based on the cycloalkanone oxime.

4. The method according to claim 1 or 2, wherein the method is employed in vaporizing a cycloalkanone oxime in which a cycloalkanone oxime remaining in a liquid state is subjected to the contact treatment.

5. The method according to claim 1 or 2, wherein the cycloalkanone oxime is in a molten state.

6. The method according to claim 1 or 2, wherein the contact is carried out in the presence of an organic solvent.

7. The method according to any one of claims 1 to 3, wherein the contact is carried out in the presence of about 30 ppm by weight or lower of a transition metal.

8. The method according to claim 7, wherein the transition metal is at least one transition metal selected from the group consisting of iron, nickel and chromium.

9. The method according to claim 7, wherein the contact is carried out at a temperature of about 50° C. or higher.

10. The method according to claim 9, wherein the contact is carried out at a temperature of about 90° C. or higher.

11. A stabilization method of a cycloalkanone oxime, which comprises the step of controlling the concentration of a transition metal in the cycloalkanone oxime to be about 30 ppm by weight or lower at a temperature of about 50° C. or higher.

12. The method according to claim 11, wherein the transition metal is at least one transition metal selected from the group consisting of iron, nickel and chromium.

13. The method according to claim 11 or 12, wherein the concentration of the transition metal is controlled at a temperature of about 90° C. or higher.

14. The method according to claim 11 or 12, herein the method is employed in vaporizing a cycloalkanone mime in which a cycloalkanone oxime remaining in a liquid state is subjected to the contact treatment.

15. The method according to claim 11 or 12, wherein the cycloalkanone oxime is in a molten state.

16. The method, according to claim 11 or 12, wherein the controlling of the concentration of the transition metal is carried out in the presence of an organic solvent.

* * * * *